United States Patent
Heilmann et al.

Patent Number: 6,053,967
Date of Patent: *Apr. 25, 2000

[54] AIR SEPARATOR

[75] Inventors: Klaus Heilmann; Bernd Knierbein, both of St. Wendel, Germany

[73] Assignee: Fresenius AG, Bad Homburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/295,430

[22] Filed: Aug. 25, 1994

[30] Foreign Application Priority Data

Sep. 1, 1993 [DE] Germany ............... 43 29 385

[51] Int. Cl.[7] ................................. B01D 19/00
[52] U.S. Cl. ............................. 96/208; 96/206; 96/216; 95/260; 95/261; 95/262; 95/267; 95/269; 210/188; 210/512.1; 210/787
[58] Field of Search ............. 95/260, 261, 262, 95/267, 269; 96/206, 208, 216, 204; 210/188, 512.1, 787; 55/463

[56] References Cited

U.S. PATENT DOCUMENTS

| | | | |
|---|---|---|---|
| 1,867,465 | 7/1932 | Moynan | 55/463 |
| 4,368,118 | 1/1983 | Siposs | 210/136 |
| 4,964,984 | 10/1990 | Reeder et al. | 210/188 |
| 5,178,656 | 1/1993 | Schott | 55/463 |

FOREIGN PATENT DOCUMENTS

| | | | |
|---|---|---|---|
| 1557029 | 4/1990 | U.S.S.R. | |
| 2041233 | 9/1980 | United Kingdom | A61M 5/16 |
| 2 063 108 | 3/1981 | United Kingdom | B04C 5/107 |
| 2063108 | 6/1981 | United Kingdom | B04C 5/107 |

OTHER PUBLICATIONS

Database WPI, Week 8645, Nov. 20, 1986, Derwent Publications Ltd., London, GB; AN 86–297435/45 & SU–A–1 219 112 (Chelyabinskpoly) März 23, 1986.

Primary Examiner—Fred Teskin
Attorney, Agent, or Firm—Henderson & Sturm LLP

[57] ABSTRACT

An air separator for liquid containing gas bubbles having an essentially cylinder-shaped chamber through which liquid, such as blood, flows essentially in helical flow paths, with the result that air bubbles are driven in a radial direction relative to the longitudinal axis of the chamber because of pressure differences produced by centrifugal forces. The inlet and outlet of the chamber of the air separator are coaxial relative to each other in the longitudinal axis of the chamber. The air separator also includes a flow-deflection component or influx distributor, which includes a rotation-symmetrical base body element whose outer surface faces inflowing liquid as a first deflection surface, which is geometrically defined by rotation of a curve section about the longitudinal axis of the chamber. The first deflection surface has deflection surface deflector vanes, which are curved in planes perpendicular relative to the longitudinal axis of the chamber, with the result that axially inflowing liquid is deflected so that desired helical flow development is induced.

27 Claims, 3 Drawing Sheets

AIR SEPARATOR

FIELD OF THE INVENTION

The invention relates to an air separator for liquid containing gases which is guided through a pipe, in particular for the separation of air bubbles from blood, with an essentially circular cylinder-shaped chamber which is flowed through by the liquid essentially on helical flow paths, with the result that the gas bubbles are driven in radial direction relative to the longitudinal axis of the chamber because of the pressure differences produced by the occurring centrifugal forces. Such a generic air separator also has an inlet and an outlet, by means of which it can be connected to a pipe, for example in the form of a tube.

DISCUSSION OF BACKGROUND AND MATERIAL INFORMATION

Such an air separator which—insofar as it is also used for gases other than air—is more generally also called a degassing device, is known for example from the laid open British patent application 2 063 108. The air separator described there has an essentially circular cylinder-shaped, perpendicularly arranged chamber to whose upper end an inlet is so arranged that the liquid to be degassed enters essentially tangentially in the area of the outer periphery. Because of the tangential introduction, the liquid to be degassed flows firstly on a circular flow path which is however overlaid by the total flow through the perpendicular chamber, with the result that the liquid flows through the chamber on a helical flow path. A tangentially arranged outlet is appropriately provided at the lower end, so that the degassed liquid can emerge. The degassing effect is effected in the case of the generic air separator or the degassing device through the creation, by the circular movement elements of the liquid flow, of centrifugal forces which build up pressure differences in the liquid, with the result that the less dense, i.e. lighter air bubbles are driven to the centre of the chamber and rise along the longitudinal axis of the chamber until they are removed through a ventilation bore.

The described air separator is used in particular for the degassing of blood. It is necessary to separate blood from possibly contained gases whenever blood is removed from the natural blood circulation of a patient and is guided by an artificial blood circulation before it is guided back again into the body of the patient. This occurs for example during cell separation within the framework of the autotransfusion of blood during operations, also during haemodialysis or haemofiltration, and in mixed forms of these treatment techniques.

In particular during the degassing of blood, the problem arises that, although on the one hand the separation of contained air bubbles must take place with great reliability, as air bubbles possibly remaining in the blood can lead to the death of the patient, on the other hand the air separator must however be so composed as regards its mechanical properties and the developed flow form that damage to the blood constituents is avoided. A good wash-out behaviour of the air separator is desirable for a low level of blood damage, which goes along with smooth surfaces on the material side and with a flow-favourable continuous structure of the flow paths, with the result that the adhesion of blood corpuscles to surfaces of the air separator and thus a conglomeration of blood corpuscles is avoided. Short residence times of the blood in the air separator are also conducive to a low level of blood damage, but without making the air separation as such worse, plus a small fill volume.

For air separators used in hospitals, it is also desirable that they can be easily secured and can be fitted without great outlay into already existing tube lines. For this reason it is desirable that inlet and outlet are arranged aligning coaxially with each other, so that the air separator can, for example after the cutting open of an existing tube, be fitted into the latter without having to change the tube guidance. Furthermore, the tube guidance at dialysis machines can for example can take place without unnecessary loops and the production process for a prefabricated unit consisting of air separator and tube is simplified, as the tubes can be assembled automatically.

In all systems affecting the safety of a patient, a constant checking facility is also desirable, so that an optical monitoring of the fill level is to be possible. Capacitive fill-level monitoring systems are also conceivable, for whose proper functioning a good wash-out behaviour is again necessary, in order to prevent residual blood from remaining in the air separator.

The air separator known from the cited British patent application only partially meets the requirements cited above. In particular, it has no coaxial connections or sockets lying in the longitudinal direction of the chamber, with the result that it is awkward to handle and the wash-out behaviour does not meet a high level of requirements.

Since, on the other hand, the helical flow development guarantees a good air separation, the object of the invention is first to provide an air separator which retains the advantages of the helical flow guidance and nevertheless makes possible connections or sockets, arranged coaxial relative to one another, lying in the longitudinal axis of the air separator.

In particular when using a generic air separator for the treatment of blood, it is desirable in the hospital sector if the air separator itself is designed as a disposable part, i.e. if it can be replaced and disposed of after a certain period of use and in particular naturally after a change of patient, as a cleaning which would satisfy the hygiene requirements of the hospital would not be justifiable in terms of outlay. A further object of the present invention is therefore to realize the advantages described above which are to be achieved by means of a newly to be created air separator, in such a way that the proposed air separator is producible at favourable cost in large numbers from customary plastics, in particular by injection moulding.

SUMMARY OF THE INVENTION

The achievement of the object in the case of a generic air separator is characterized in that inlet and outlet are arranged lying in the longitudinal axis of the chamber, and, to produce the helical flow pattern, there is arranged downstream from the inlet a flow-deflection component—also called influx distributor hereinafter—which essentially consists of a rotation-symmetrical round body whose outer surface facing the inflowing liquid (also called first deflection surface) is geometrically defined by rotation of a curve section about the longitudinal axis of the chamber, and in that there are arranged on the deflection surface deflector vanes which, to produce the circular movement elements of the flow, are curved in planes standing perpendicular on the longitudinal axis of the chamber. The curve section is preferably an ellipse section.

Because of the use according to the invention of a flow-deflection component (influx distributor) arranged downstream from the inlet, it is made possible to provide an arrangement of inlets and outlets in the longitudinal axis of the chamber without having to forgo the advantages of the basic concept of giving the flow a helical development and using the occurring centrifugal forces to degas the blood. Through the described structure of the influx distributor, it is ensured on the one hand that this component, because of its geometric shape, can easily be made from customary plastics, in particular transparent ones, in the injection moulding process, while on the other hand a continuous flow guidance which largely avoids impacts is made possible, with the result that a uniform flow profile is produced in the blood or in the other liquid to be degassed where appropriate, which goes along with low and uniform shearing stresses and accordingly a low level of damage to the blood.

Particularly advantageous in this case is a design of the rotation-symmetrical base body of the influx distributor in which the outer surface or the first deflection surface is defined by rotation of a concavely curved curve section about the longitudinal axis of the chamber. An impact-free influx of the blood into the air separator is encouraged by such a design.

On the other hand it can be provided to design the rotation-symmetrical base body of the influx distributor in the form of a cone. Such a design of the influx distributor does mean somewhat higher impact losses in the influx zone, but offers, besides manufacturing advantages, the further advantage that the mouth of a dip tube can be arranged in the inside of the cone, which opens up the possibility of designing the air separator for a throughflow from the bottom upwards.

It is also advantageous to provide a second deflection surface arranged parallel to the first, the height of the deflector vanes then being preferably so dimensioned that they extend perpendicular to the flow direction from one deflection surface to the other. In each case two deflector vanes and the two deflection surfaces arranged parallel to each other then each define a flow channel through which the flow can be more precisely guided and flow separations, the inducing of eddies etc. can be prevented. Such a design also helps to avoid eddyings with the high shearing stresses associated with them, with the result that the design is advantageous in particular from the viewpoint of as minimal as possible a level of damage to the blood.

With the already described arrangement of the air separator structured so that it is flown through from the bottom upwards, it can advantageously be provided that the outside wall of the chamber is designed as a cone sectionwise and the inside of the wall simultaneously functions as a second deflection surface.

Further advantages and features of the air separator according to the invention are described in more detail in the following with reference to embodiments represented in the drawings.

DETAILED DESCRIPTION

Figure 1:
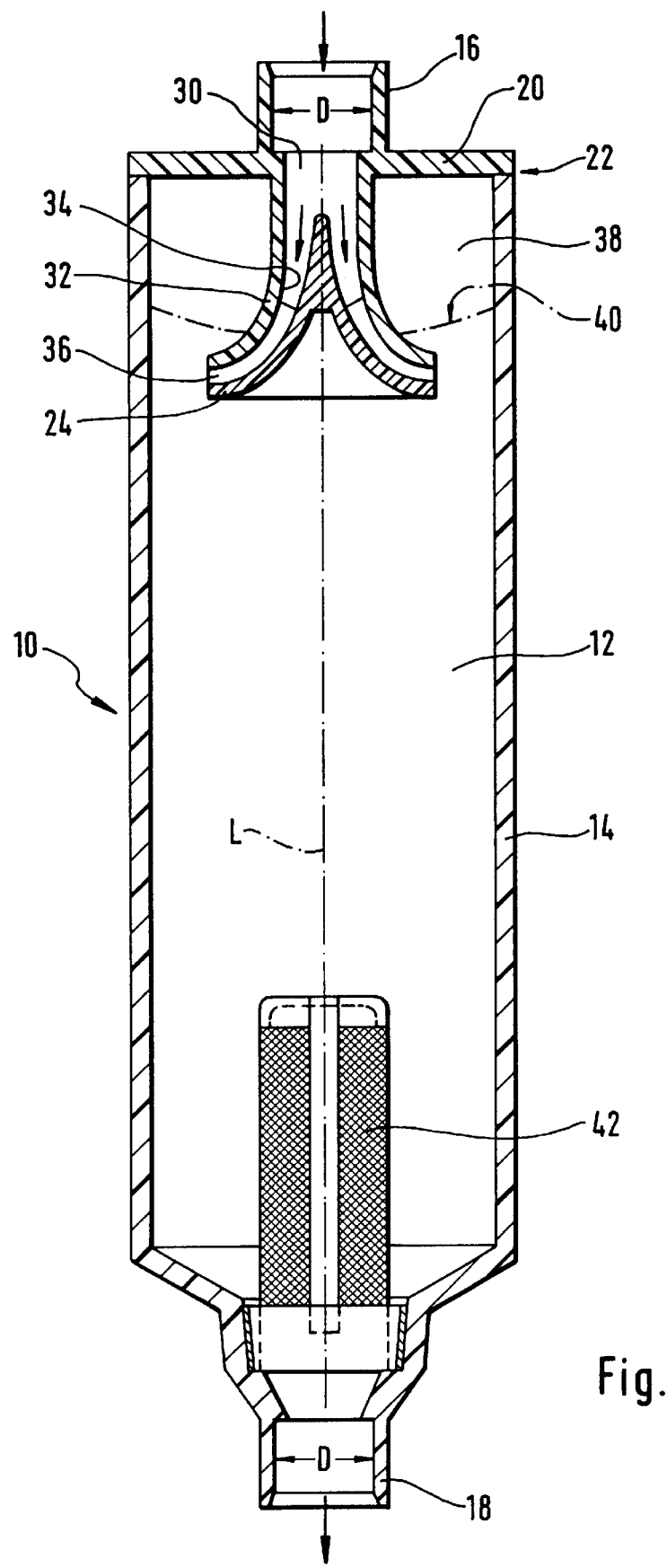
FIG. 1 a longitudinal section through a perpendicularly arranged air separator according to a first version of the invention, which is proposed for a through-flow direction from the top downwards, FIG. 2 a perspective representation of the flow distributor with a second deflection surface fitted, FIG. 3 a perspective view of the influx distributor from FIG. 2 with the second deflection surface removed, FIG. 4 a plan view of the influx distributor according to FIG. 3, and FIG. 5 a longitudinal section through an air separator according to a second version of the invention, which is designed for a throughflow from the bottom upwards.

Represented in longitudinal section in FIG. 1 is an air separator 10 according to the invention, which essentially consists of a perpendicularly arranged circular cylinder-shaped chamber 12 which is bounded by a wall 14. An inlet 16 is arranged at the upper end of the chamber 12 and an outlet 18 at the lower end, each having an internal diameter D which together with the diameter of a tube to be inserted forms a compression fit. The inlet 16 is designed in one piece with a cover component 20 which is produced as a plastic part in the injection moulding process and is connected to the wall 14, likewise produced in the injection moulding process, of the chamber 12 by welding or the like at a seam joint 22.

Figure 3:
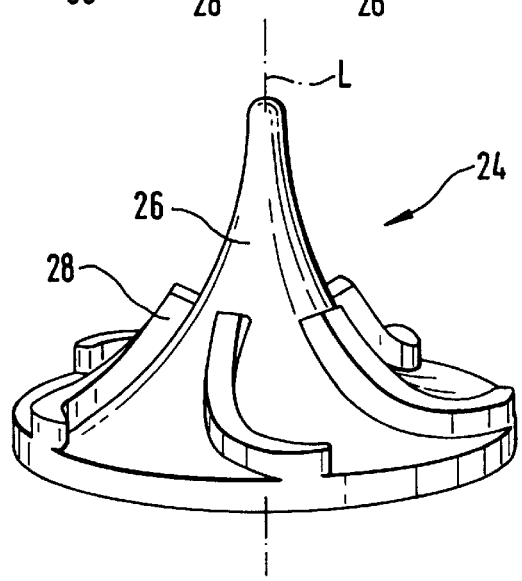
Figure 4:
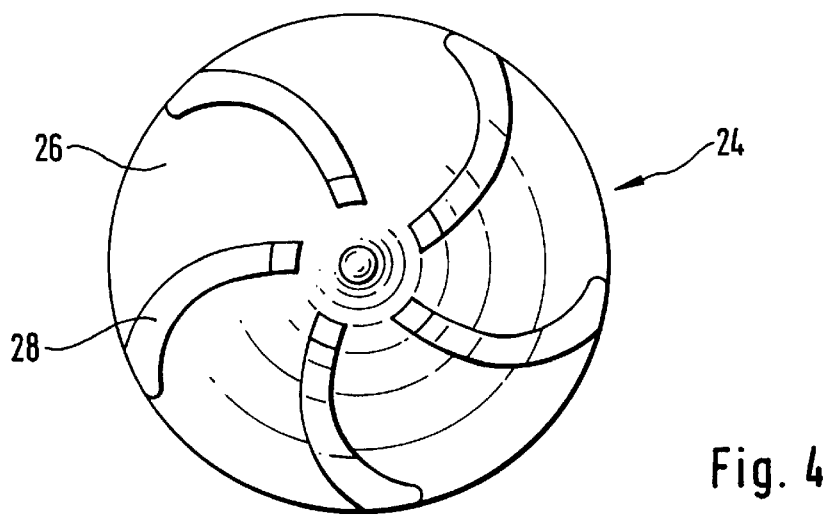

Arranged downstream from the inlet 16 is an influx distributor 24 which is more generally called a flow-deflection component within the framework of this description. The influx distributor 24 is represented perspectively in FIG. 3. It consists of a rotation-symmetrical base body 26, whose outer surface facing the inflowing liquid is called the first deflection surface. This first deflection surface is geometrically defined by rotation of a concave curve section about the longitudinal axis L of the chamber. Arranged on the first deflection surface are deflector vanes 28 which follow the concave curvature of the deflection surface of the rotation body 26. The deflector vanes are additionally, as illustrated in FIG. 4, curved in planes which stand perpendicular on the longitudinal axis L of the chamber. Through this design of the deflector vanes 28, the liquid flowing into the inlet 16 in the direction of the upper arrow in FIG. 1 is initially deflected radially outwards by the concave curvature of the base body 26 and additionally deflected by the curvature of the vanes 28 in planes standing perpendicular on the longitudinal axis, with the result that, upon leaving the influx distributor 24, the liquid flows essentially tangentially relative to the circular wall 14 of the chamber 12, whereby the desired helical flow is induced.

Figure 2:
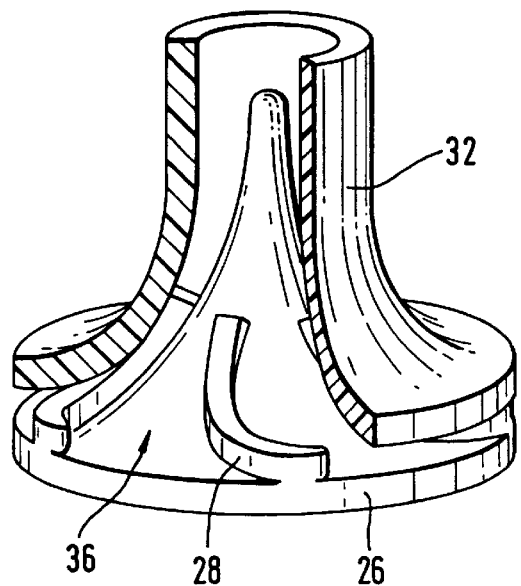

As FIG. 1 shows, additional to the inlet 16 which is designed in one piece with the cover component 20, there is, downstream from an inflow aperture 30, a further flange 32 designed in one piece with the cover component 20, whose inner surface 34 is arranged as a second deflection surface parallel to the first deflection surface of the influx distributor 24. The influx distributor 24 is likewise produced in the injection moulding process and welded to the second deflection surface 34 via the upper sides 36 of the deflector vanes 28 or secured by a clamp connection. The diameter of the inlet aperture 30 is preferably so chosen that it corresponds to the internal diameter of the tube to be introduced into the inlet 16, with the result that no edges causing a flow separation remain, but rather a smooth transition results between the inside of the tube to be supplied and the second deflection surface 34. The second deflection surface 34 bounds together with the first deflection surface of the base body 24 an essentially annular gap which is divided into flow channels by the deflector vanes 28 (cf. FIG. 3). The flow channels 36 are to be seen particularly clearly in FIG. 2, which shows the base body 26, the deflector vanes 28 and the flange 32. The flange 32 is shown as an independent individual part, however it is preferably provided that, as can be seen from FIG. 1, it is designed in one piece with the cover component 20.

The inflowing blood or the other liquid to be degassed passes through the inlet 16 and flows through the flow-deflection channels 36, as a result of which the flow direction is deflected in a spatially wound curve out of the direction initially running parallel to the longitudinal axis 11 into a direction running tangentially against the wall 14 of the chamber 12. A helical flow is thereby induced, with the circular movement elements building up a pressure difference, the result of which is that the air bubbles are driven in the direction of the longitudinal axis and, because of their lower density, climb upwards. The risen air bubbles form, in the upper part of the chamber 12, an air cushion 38 which can be removed through a suitable ventilation bore not represented in FIG. 1. The liquid surface 40 of the blood which has flown in has a slightly parabolic shape because of the rotation, the parabola represented in FIG. 1 being shown superelevated. In general, the lowest possible flow velocities are to be sought, in order to prevent a fresh supply of air at the surface 40 of the liquid. As FIG. 1 also shows, the outlet of the influx distributor 24 is arranged underneath the liquid surface 40.

After the blood has flowed from the top downwards in helical paths through the chamber 12, it flows through an additionally provided filter candle 42 and then through the outlet 18 for further use.

Figure 5:
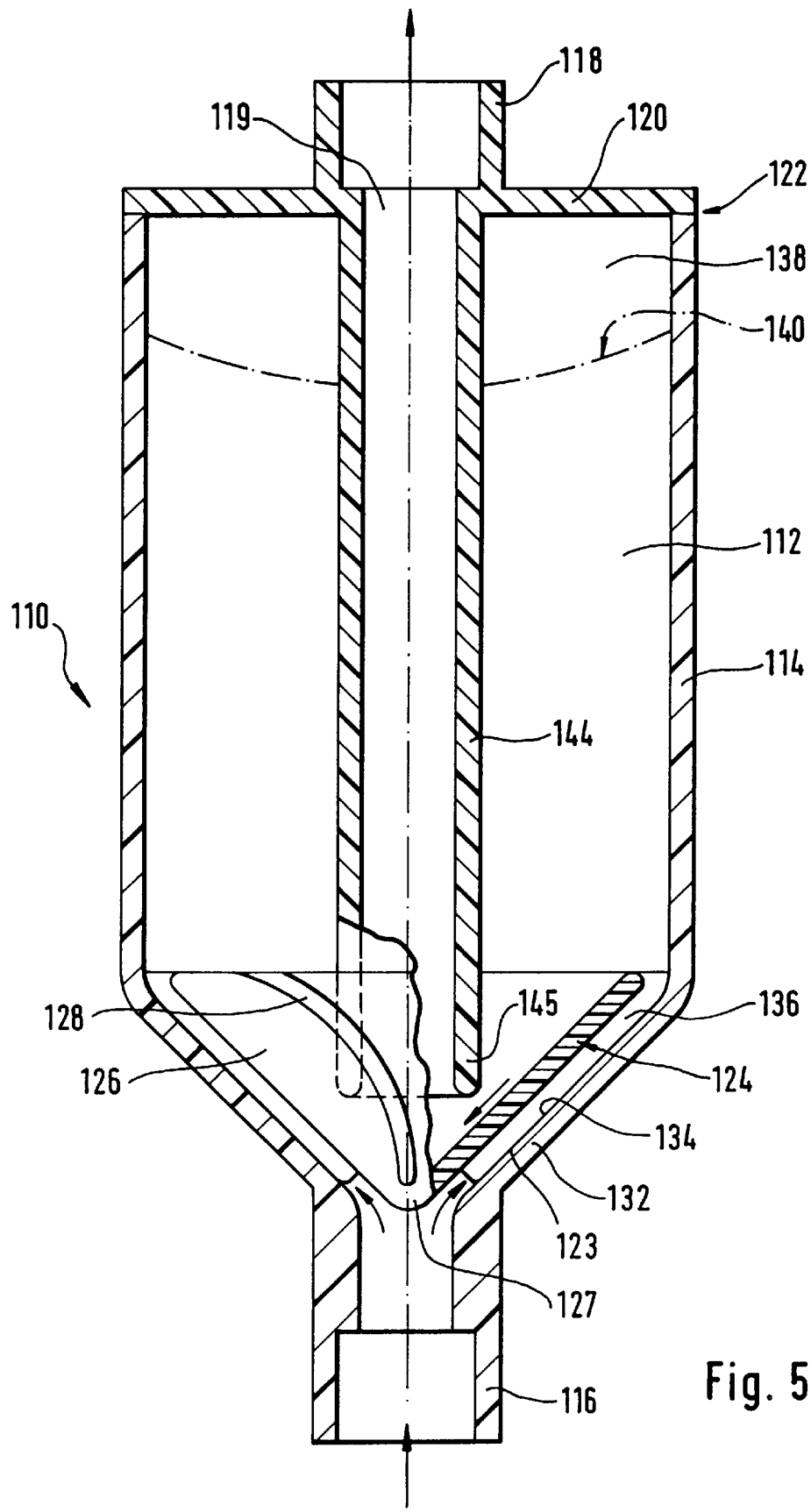

Represented in FIG. 5 is an alternative version of an air separator according to the invention, in which a chamber 112 enclosed by a wall 114 is flowed through from the bottom upwards. In the embodiment represented in FIG. 5, identical or comparable parts are given the same reference numbers, but increased by 100. In this embodiment, the influx distributor 124 has a base body 126 which is essentially conical. The consequence of this is that, when the liquid entering through the inlet 116 encounters the tip 127 of the cone, impact losses must be accepted because of the discontinuous deflection, but this version offers, besides a design favourable for production purposes, the further advantage that space remains in the inside of the cone 126 for the mouth of a dip tube 144 connected to the outflow aperture 119. The liquid entering through the inlet 116 flows initially through the flow-deflection channels 136 which, as in the embodiment discussed previously, are bounded by a first deflection surface which represents the surface of the conical base body 126 of the influx distributor 124, and in each case by two deflector vanes 128 and a second guide surface 123, which in the present embodiment is formed by a wall section 132 of the wall 114 forming the chamber. After leaving the influx distributor 124, the flow climbs upwards in helical flow lines, contained air bubbles being forced inwards by the pressure differences produced because of centrifugal forces and gathering in an air cushion 138 which—as already described previously—can be broken up by a ventilation bore, not represented, in the cover component 120.

Because of the pressure which has built up, liquid is forced through the mouth 145 of the dip tube 144 and rises in the latter, in order to flow out through the outlet 118. What is advantageous about this is that it is made possible by the deep-reaching dip tube 144 to remove blood from the flow-calmed areas of the chamber 112, which further advantageously supports the degassing. The dip tube 144 is advantageously designed together with the outlet 118 in one piece with the cover component 120 and can be manufactured in the injection moulding process. The cover component 120 is welded to the wall 114 of the chamber 112 at a joint 122. The influx distributor 124 can likewise be produced in the injection moulding process without major outlay and connected by welding or the like by means of the deflector vanes 128 to the second deflection surface 134 which forms a part of the inner surface of the chamber 112. Clamp connections can also be provided, thus for example between the deflector vanes and the dip tube. A gap of ca. 0.2 mm can remain between the upper edges of the vanes 28 and the second deflection surface lying opposite, in order to be able to rinse the upper side of the vanes, whereby inter alia a conglomeration of blood corpuscles is countered.

Both versions of the air separator according to the invention are preferably produced from transparent plastic in the injection moulding process, with the result that an optical check on the fill level and flow pattern is easily possible at all times.

Through the design according to the invention of an air separator, an air separator to be produced cheaply in large numbers is created which makes possible a rapid coaxial connection with the tubes of a blood circulation and can be disposed of after use, type-pure plastic waste being produced.

The air separator can particularly be used for all medical fluids.

Said fluids include parenteral solutions, plasma, blood or other fractions of blood.

What is claimed is:

1. An air separator for liquid containing gas bubbles comprising a chamber, said chamber comprising an inlet and an outlet arranged in a longitudinal axis of the chamber, and a flow-deflection component arranged downstream from the inlet, wherein said flow-deflection component comprises a rotational-symmetrical base body having an outer deflection surface facing inflowing liquid, said outer deflection surface being geometrically defined by rotation of a curved section about the longitudinal axis of the chamber, and deflector vanes, which are curved in planes perpendicular to the longitudinal axis of the chamber, arranged on said outer deflection surface.

2. The air separator according to claim 1, wherein the curved section is concavely curved.

3. The air separator according to claim 1, wherein the curved section comprises a substantially straight-line section, and the base body of the flow-deflection component is substantially conical.

4. The air separator according to claim 1, comprising a second flow-deflection surface arranged at a distance parallel to the outer deflection surface.

5. The air separator according to claim 4, wherein the deflector vanes comprise a height so dimensioned that the deflector vanes extend transversely to a direction of flow from the outer deflection surface to the second deflection surface.

6. The air separator according to claim 2, wherein the chamber is designed for a throughflow from the top downwards.

7. The air separator according to claim 3, wherein the chamber is designed for a throughflow from the bottom upwards.

8. The air separator according to claim 3, comprising a dip tube which extends inside of a frustoconical flow-deflection component connected to the outlet.

9. The air separator according to claim 4, wherein the outer wall of the essentially circular cylinder-shaped chamber comprises an adjoining conical area comprising an inside forming the second deflection surface.

10. The air separator according to claim 6, wherein the second deflection surface comprises part of a surface of a flange integral with a cover component.

11. The air separator according to claim 2, wherein the curved section is an ellipse section.

12. The air separator according to claim 8, wherein a dip tube secures an influx distributor.

13. The air separator according to claim 2, comprising a second flow-deflection surface arranged at a distance parallel to the outer deflection surface.

14. The air separator according to claim 3, comprising a second flow-deflection surface arranged at a distance parallel to the outer deflection surface.

15. The air separator according to claim 13, wherein the deflector vanes comprise a height so dimensioned that the deflector vanes extend transversely to a direction of flow from the outer deflection surface to the second deflection surface.

16. The air separator according to claim 14, wherein the deflector vanes comprise a height so dimensioned that the deflector vanes extend transversely to a direction of flow from the outer deflection surface to the second deflection surface.

17. The air separator according to claim 1, wherein the chamber is designed for a throughflow from the top downwards.

18. The air separator according to claim 3, wherein the chamber is designed for a throughflow from the top downwards.

19. The air separator according to claim 4, wherein the chamber is designed for a throughflow from the top downwards.

20. The air separator according to claim 5, wherein the chamber is designed for a throughflow from the top downwards.

21. The air separator according to claim 1, wherein the chamber is designed for a through flow from the bottom upwards.

22. The air separator according to claim 2, wherein the chamber is designed for a through flow from the bottom upwards.

23. The air separator according to claim 4, wherein the chamber is designed for a through flow from the bottom upwards.

24. The air separator according to claim 5, wherein the chamber is designed for a throughflow from the bottom upwards.

25. The air separator according to claim 7, comprising a dip tube which extends inside of a frustoconical flow-deflection component connected to the outlet.

26. The air separator according to claim 7, wherein the outer wall of the essentially circular cylinder-shaped chamber comprises an adjoining conical area comprising an inside forming the second deflection surface.

27. The air separator according to claim 8, wherein the outer wall of the essentially circular cylinder-shaped chamber comprises an adjoining conical area comprising an inside forming the second deflection surface.

* * * * *